United States Patent [19]

Phillipps et al.

[11] 4,353,898

[45] Oct. 12, 1982

[54] 11α-AMINO-ANDROSTANES

[75] Inventors: Gordon H. Phillipps, Wembley; David C. Humber, Ealing; George B. Ewan, Northolt; Barry A. Coomber, Pinner, all of England

[73] Assignee: Glaxo Group Limited, London, England

[21] Appl. No.: 283,454

[22] Filed: Jul. 15, 1981

[30] Foreign Application Priority Data

Jul. 16, 1980 [GB] United Kingdom ............... 8023295
Dec. 9, 1980 [GB] United Kingdom ............... 8039383
Mar. 2, 1981 [GB] United Kingdom ............... 8106487
May 29, 1981 [GB] United Kingdom ............... 8116413

[51] Int. Cl.³ ............................................. A61K 31/56
[52] U.S. Cl. .................................. 424/238; 260/397.1
[58] Field of Search .................................. 260/397.1; /Steroids MS File; 424/238

[56] References Cited

U.S. PATENT DOCUMENTS 2,982,775  5/1961  Oliveto et al. ................ 260/397.45
3,064,013 11/1962  Babcock et al. ............... 260/397.3
3,215,713 11/1965  Barton .......................... 260/397.4
3,256,331  6/1966  Jones et al. .................... 260/566
3,558,673  1/1971  Ruggieu et al. ................ 260/397.1
3,943,124  3/1976  Phillipps et al. ............... 260/397.1

FOREIGN PATENT DOCUMENTS 853227  4/1977  Belgium ........................ 260/397.45
878069  9/1961  United Kingdom ........... 260/397.45
887815  1/1962  United Kingdom ........... 260/397.45
924421  4/1963  United Kingdom ........... 260/397.45
1439605 6/1976  United Kingdom ........... 260/397.45

OTHER PUBLICATIONS

Campbell et al., (J C S Perkin I (1979), 1936–1940).
Hershbert et al., (Chem. and Ind., 1958, 1477–1478).
Rausser et al., J. Org. Chem., 1966, 31 (5) 1342–1346 and 1346–1349.
Gratz and Rosenthal (Steroids, 1969, 14 (6), 739–753).
Pelah et al., (JACS. 1965, 87 (3), 574–580).
Marples (JCS Perkin I, 1974 (19), 2219–2225).

Primary Examiner—Elbert L. Roberts
Attorney, Agent, or Firm—Bacon & Thomas

[57] ABSTRACT

Compounds of formula

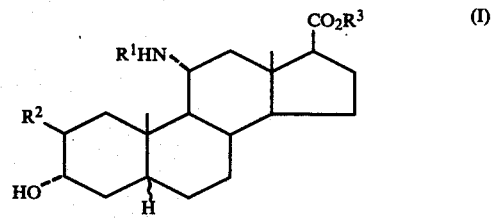

wherein:
$R^1$ is a $C_{1-8}$ alkyl group or a $C_{3-7}$ cycloalkyl group;
$R^2$ is a hydrogen atom, a $C_{1-6}$ alkoxy group or a $C_{2-5}$ alkanoyloxy group; and
R is a $C_{1-8}$ alkyl group or a $C_{3-7}$ cycloalkyl group;
provided that when the compounds contain a 5β-hydrogen atom, $R^2$ is a hydrogen atom, and the D-homo analogues thereof having the group —$CO_2R^3$ (wherein $R^3$ is as defined above) at the 17aβ-position, and salts thereof have activity as antidysrhythmic agents and may be applicable for treatment of ventricular dysrhythmias in humans or animals. The compounds may be provided in the form of compositions in admixture with pharmaceutical carriers and excipients and may be prepared by a variety of processes known for producing steroids of this type. The invention also provides intermediates for the preparation of the compounds of formula (I), wherein $R^3$ and/or $R^1$ are replaced with hydrogen atoms, and processes for the preparation of such intermediates.

13 Claims, No Drawings

11α-AMINO-ANDROSTANES

This invention relates to aminosteroids having antidysrhythmic activity, and in particular to certain compounds in the androstane series having a substituted amino group at the 11α-position.

The aim of antidysrhythmic therapy is to return hazardous abnormal heart rhythms towards normal, or to reduce the likelihood of hazardous rhythms developing in patients at risk as a result of hypertension, atheromas, diabetes or heart conditions such as myocardial disease, ischaemia or infarction.

It is recognised that dysrhythmias in patients with heart attack and other conditions are treatable and preventable. There are several drugs available for the treatment of ventricular dysrhythmias but their application is limited by their lack of efficacy or by their toxicity which gives rise to various side effects.

Thus there is a demand for drugs suitable for use in the treatment of patients with dysrhythmias, and therefore in danger of sudden cardiac death. Furthermore, there is a demand for such drugs for administration, for example for long term prophylaxis, to patients at risk of developing dysrhythmias, in which case, activity on oral administration is desirable.

In Belgian Patent Specification No. 853227 there is described a group of 11α-tertiary amino-3α-hydroxy steroids having anaesthetic activity. In addition to the 11α-tertiary amino and 3α-hydroxy groups, the possibility of the compounds possessing various substituents in other positions including the 17β-position is allowed for, one possible 17β-substituent being a $C_{1-5}$ alkoxycarbonyl group. Corresponding 11α-primary and secondary amino steroids are also described as intermediates for the preparation of the tertiary amino compounds. There is no specific disclosure in Belgian Pat. No. 853227 of any 11α-primary or secondary amino-17β-alkoxycarbonyl compounds, and no anaesthetic activity is ascribed to any such compounds specifically. Furthermore, no antidysrhythmic activity has been ascribed to any of the compounds in the above Belgian Patent Specification, or indeed to any compounds of comparable structure.

We have now discovered that a group of 11α-secondary amino-3α-hydroxy steroids having a 17β-carboxylic ester group have surprisingly high antidysrhythmic activity while lacking general anaesthetic activity. The antidysrhythmic activity of the compounds is significantly greater than that possessed by the analogous compounds specifically disclosed in Belgian Patent Specification No. 853227, having other 17β-groups. The compounds thus have potential for use as antidysrhythmic drugs.

Accordingly the invention provides compounds of the formula

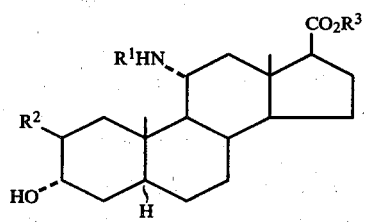

wherein $R^1$ is a $C_{1-8}$ alkyl group or a $C_{3-7}$ cycloalkyl group;

$R^2$ is a hydrogen atom, a $C_{1-6}$ alkoxy group or a $C_{2-5}$ alkanoyloxy group; and $R^3$ is a $C_{1-8}$ alkyl group or a $C_{3-7}$ cycloalkyl group; (provided that when the compounds contain a 5β-hydrogen atom, $R^2$ is a hydrogen atom) and the D-homo analogues thereof having the group —$CO_2R^3$ (wherein $R^3$ is defined above) at the 17aβ-position, and acid addition salts thereof.

Where $R^1$ or $R^3$ is a cycloalkyl group it may be for example a cyclopropyl, cyclobutyl, cyclopentyl, cyclohexyl or cycloheptyl group.

Where either of the groups $R^1$ and $R^3$ is an alkyl group, such a group may be straight or branched-chained.

Where $R^1$ is an alkyl group, it preferably has 3–7 carbon atoms, and may for example be a propyl, butyl, pentyl, isopentyl, hexyl, isohexyl or neohexyl group. Where $R^2$ is an alkoxy group it may be for example a methoxy, ethoxy, propoxy, butoxy, pentyloxy or hexyloxy group; an example of an alkanoyloxy group is the acetoxy group. Where $R^3$ is an alkyl group it may for example be a methyl, ethyl, propyl, isopropyl, butyl or isopentyl group.

The total number of carbon atoms in the groups $R^1$, $R^2$ and $R^3$ together is preferably from 3 to 10 carbon atoms.

$R^3$ is preferably a $C_{1-8}$ alkyl group, and where compounds having good activity on oral administration are desired, $R^3$ is preferably a methyl or ethyl group.

Ring D conveniently has five members.

The compounds preferably have a 5α-hydrogen atom.

Preferred compounds are 5α-androstanes having five members in ring D in which: $R^1$ is an isopentyl, hexyl, isohexyl, neohexyl, cyclopentyl or cyclohexyl group; $R^2$ is a hydrogen atom or a methoxy, ethoxy or propoxy group, especially a methoxy or ethoxy group; and $R^3$ is a methyl or ethyl group, especially a methyl group.

The compounds of formula (I) may form acid addition salts; physiologically acceptable salts are preferred. Examples of such salts are hydrochlorides, hydrobromides, phosphates, sulphates, p-toluenesulphonates, methanesulphonates, citrates, tartrates, acetates, ascorbates, lactates, maleates, succinates, tricarballylates, glutarates and glutaconates. The hydrochlorides are preferred acid addition salts.

Individual compounds which are preferred on the basis of their high antidysrhythmic activity include:
1. methyl 2β-ethoxy-3α-hydroxy-11α-(3-methylbutylamino)-5α-androstane-17β-carboxylate,
2. methyl 2β-methoxy-3α-hydroxy-11α-(3-methylbutylamino)-5α-androstane-17β-carboxylate,
3. methyl 11α-cyclohexylamino-2β-ethoxy-3α-hydroxy-5α-androstane-17β-carboxylate,
4. methyl 11α-(3,3-dimethylbutylamino)-2β-ethoxy-3α-hydroxy-5α-androstane-17β-carboxylate,
5. methyl 11α-cyclohexylamino-3α-hydroxy-2β-methoxy-5α-androstane-17β-carboxylate,
6. methyl 3α-hydroxy-11α-(3-methylbutylamino)-5α-androstane-17β-carboxylate,
7. methyl 11α-cyclohexylamino-3α-hydroxy-5α-androstane-17β-carboxylate,
8. methyl 11α-cyclopentylamino-3α-hydroxy-5α-androstane-17β-carboxylate,
9. methyl 3α-hydroxy-11α-(3-methylbutylamino)-2β-propoxy-5α-androstane-17β-carboxylate, 10. methyl 2β-ethoxy-11α-hexylamino-3α-hydroxy-5α-androstane-17β-carboxylate,
11. methyl 11α-cyclopentylamino-3α-hydroxy-2β-methoxy-5α-androstane-17β-carboxylate,
12. ethyl 2β-ethoxy-3α-hydroxy-11α-(3-methylbutylamino)-5α-androstane-17β-carboxylate,
13. methyl 11α-cycloheptylamino-3α-hydroxy-2β-methoxy-5α-androstane-17β-carboxylate and
14. methyl 11α-cyclobutylamino-3α-hydroxy-2β-methoxy-5α-androstane-17β-carboxylate and their physiologically acceptable acid addition salts, e.g. their hydrochlorides.

A highly preferred member of this group is compound 1 and its physiologically acceptable acid addition salts such as the hydrochloride salt. Investigations both in vitro and in experimental animals have shown that this compound possesses a highly desirable combination of pharmacological properties. In particular, against aconitine-induced dysrhythmias an anaesthetised rats the compound exhibited high levels of activity following both oral and intravenous administration. The oral and intravenous therapeutic indices were high and a single oral dose of the compound gave a prolonged duration of action. The compound was highly effective in reducing the mortality and the incidence and duration of ventricular bigeminy, tachycardia and fibrillation in coronary artery-ligated anaesthetised rats. The compound was effective, when administered intravenously or orally, against post-infraction dysrhythmias in the conscious dog.

Other compounds possessing similar properties to compound 1 are compounds 2, 5 and 7.

The compounds may be used in the treatment of patients with disturbances of cardiac rhythm, whether arising spontaneously, or as a result of treatment with other drugs, e.g. cardiac glycosides, or as a consequence of myocardial ischaemia or infarction. Alternatively, they may be used for the prophylactic treatment of patients at risk of cardiac rhythm disturbances or sudden coronary death.

The invention accordingly further provides compounds of formula (I) and their physiologically acceptable acid addition salts for use in the therapy or prophylaxis of cardiac dysrhythmias in a human or animal subject. The invention also provides compounds of formula (I) and their physiologically acceptable acid addition salts in association with instructions for their use in the therapy or prophylaxis of cardiac dysrhythmias in a human or animal subject.

As a further aspect of the invention there are provided compounds of the formula

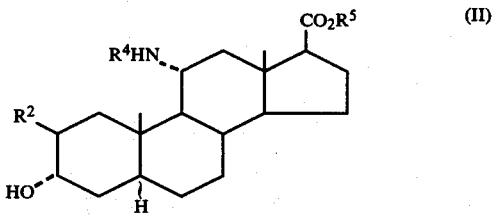

(II)

(wherein $R^2$ is as hereinbefore defined (provided that when the compounds contain a 5β-hydrogen atom, $R^2$ is a hydrogen atom), $R^4$ is a hydrogen atom or a group $R^1$ as hereinbefore defined and $R^5$ is a hydrogen atom or a group $R^3$ as hereinbefore defined, provided that at least one of $R^4$ and $R^5$ is a hydrogen atom) and the D-homo analogues thereof having the group —$CO_2R^5$ at the 17aβ-position, and salts and zwitterionic forms thereof.

The compounds of formula (II) may form acid addition salts. The compounds of formula (II) in which the group —$CO_2R^5$ represents a carboxyl group may also form salts with bases or exist as zwitterions.

Examples of acid addition salts are those given above in connection with the compounds of formula (I). The salts with bases may be salts with inorganic bases such as alkali metal salts, e.g. sodium, potassium and lithium salts; alkaline earth metal salts, e.g. calcium and magnesium salts; and ammonium salts, or salts with organic bases for example amine salts.

Compounds of formula (II) are useful as intermediates in the preparation of compounds of formula (I) using the methods described hereinafter.

The compounds of the invention may be prepared by a number of different methods, using generally known techniques. Suitable methods are described below:

1. A substituent on the 11α-amino function may be introduced by reacting the corresponding 11α-amino compound, i.e. a compound of formula (II) in which $R^4$ is hydrogen, with a compound of the formula $R^1X$ wherein X is a readily displaceable atom or group such as a halide (e.g. iodide), a hydrocarbylsulphonyloxy group (e.g. toluene-p-sulphonyloxy), a hydrocarbyloxysulphonyloxy group (e.g. methoxysulphonyloxy) or a dialkoxyphosphonyloxy group (e.g. dimethoxyphosphonyloxy). When carried out on compounds of formula (II) in which $R^5$ is also hydrogen, such a reaction may result in esterification to form a compound of formula (I) in which $R^1=R^3$. The group $R^3$ may, if not desired in the final product, subsequently be replaced by transesterification, for example as set out under 8. below. The introduction of the substituent on the 11α-amino function is preferably carried out in the presence of a base (e.g. potassium carbonate or silver oxide) in solution at any suitable temperature from ambient to reflux (e.g. +20° to +100° C.). The reaction is conveniently effected in a suitable reaction solvent. Suitable solvents include ethers (e.g. dioxan), substituted amides (e.g. N,N-dimethylformamide or N,N-dimethylacetamide), sulphoxides (e.g. dimethylsulphoxide), alkanols (e.g. ethanol or methanol) or acetonitrile.

When X is a chlorine or bromine atom, the reaction may be facilitated by addition of an iodide such as sodium iodide.

Compounds of formula (II) wherein $R^4$ is hydrogen may be prepared by reduction of the corresponding 11-oxime. Such a reduction may be effected with an alkali or alkaline earth metal in an alcohol and/or an amine and/or ammonia, e.g. sodium in n-propanol, if desired in the presence of a suitable solvent, e.g. tetrahydrofuran, at any suitable temperature up to and preferably at reflux.

The 11-oximes may themselves be prepared from the corresponding 11-oxo compounds. The 11-oxo compound may for example be reacted with hydroxylamine under strongly alkaline conditions in aqueous alcohol (e.g. ethanol), preferably at reflux. The reaction may also be carried out under acidic conditions (ca. pH 4), e.g. in buffered pyridine.

The severe conditions used in the reduction of the 11-oxime make it necessary or desirable that certain substituents for example the 17β-alkoxycarbonyl substituent and a 2β-alkanoyloxy substituent where required should be introduced after the formation of the 11α-amino group.

2. Opening of a corresponding 2α,3α-epoxide.

This reaction may be used to prepare 2β-substituted 5α-compounds. The general method of preparing 2β-compounds by this route is described in our British Patent Specification No. 1376892. Thus in general the reaction comprises treating the corresponding 2α,3α-epoxide with a compound $HR^2$ under acidic conditions (if necessary in the presence of an added acid catalyst, e.g. sulphuric acid, perchloric acid or boron trifluoride etherate) or a compound which produces the anion $(R^2)^-$ (where $R^2$ is as defined above, other than hydrogen), and then (when the initial product possesses a deprotonated 3α-hydroxy group) treating the product with a source of protons (e.g. aqueous ammonium chloride) to form the 3α-hydroxy group. Examples of $HR^2$ reagents are alcohols and carboxylic acids. Examples of reagents which produce $(R^2)^-$ anions are alkali metal or ammonium salts of $HR^2$ acids and alkali metal alkoxides. The reaction is preferably carried out under anhydrous conditions at any suitable temperature up to reflux.

The reaction may be carried out in a suitable solvent medium (e.g. a hydrocarbon, halogenated hydrocarbon or ether) or, when the reagent is a compound $HR^2$, an excess of the reagent may be used as the reaction solvent.

The starting materials required for this reaction may for example be prepared by first introducing the desired 11α-amino group (e.g. by the method of reaction 1 above) using a $\Delta^2$—starting material, then forming a salt (e.g. with toluene-p-sulphonic acid) and then epoxidising the $\Delta^2$—compound with a peracid, finally regenerating the free base. $\Delta^2$—Compounds may be prepared by formation of the 3-methanesulphonate and subsequent elimination of methanesulphonic acid.

This reaction may also be used to make the intermediates of formula (II), but when the epoxidation is effected in the presence of a primary or secondary 11α-amino group the amino group may also be protected for example as a trichloroethoxycarbonyl derivative. The trichloroethoxycarbonyl group can be removed subsequently by hydrolysis with alkali or preferably by reduction with zinc and acetic acid.

3. A corresponding 11α-amino compound, i.e. a compound of formula (II) in which $R^4$ is hydrogen can be reductively "alkylated" with a monocarbonyl compound serving to introduce the group $R^1$, in the presence of a reducing agent, the term "alkylated" being used to refer to the introduction of a cycloalkyl group as well as an alkyl group. The reducing agents which may be used are those generally known for the reduction of imines, examples being formic acid (e.g. at any suitable temperature up to 100°-120° C., for example from room temperature up to 100°, and using the carbonyl compound as the reaction solvent, in the presence or absence of water), an alkali metal borohydride or cyanoborohydride (e.g. sodium borohydride or cyanoborohydride, using an alcohol such as ethanol as solvent, suitably at room temperature), iron pentacarbonyl or an alkali metal hydrogen iron carbonylate (e.g. Fe(CO)$_5$ or MHFe(CO)$_4$ where M is sodium or potassium, at any suitable temperature up to reflux using an ether such as tetrahydrofuran or an alcohol or aqueous alcohol as solvent), hydrogen in the presence of a metal catalyst (using an alcohol, e.g. ethanol, an ether, e.g. dioxan or an ester, e.g. ethyl acetate, as reaction solvent, conveniently at room temperature), or aluminium amalgam in the presence of water (conveniently at room temperature, and in the presence of an ether solvent such as tetrahydrofuran).

The metal catalyst may, for example, be a noble metal catalyst such as platinum, platinum oxide, palladium or rhodium. The catalyst may be supported, e.g. on charcoal or kieselguhr. A homogeneous catalyst such as tristriphenylphosphine rhodium chloride may also be used. If desired the intermediate imino compound may be isolated.

Thus, for example, the use of formaldehyde, acetaldehyde, 3-methylbutanal or cyclohexanone can provide the 11α-N-methyl, N-ethyl, N-iso-pentyl or N-cyclohexyl amines respectively. It will be appreciated that the conditions should be chosen to give predominantly the desired N-monosubstituted compound, and minimise production of the corresponding N,N-disubstituted compound. Reductive alkylation of the compounds of formula (II) in which $R^4$ and $R^5$ are both hydrogen atoms is preferably effected under basic conditions.

4. Reduction of a corresponding 3-oxo compound.

2β-Unsubstituted steroids of the invention may be prepared from appropriate 3-oxo compounds by stereospecific reduction. 5α-compounds may be prepared by the method of Browne and Kirk (J.Chem.Soc. C, 1969, 1653) or by the method of our British patent specification No. 1409239. The latter method preferably uses a pre-formed iridium catalyst reduction system. For example, a reduction system may be prepared from an iridium acid or salt (e.g. chloroiridic acid), a trivalent phosphorus compound such as a phosphorous acid ester (e.g. trimethyl phosphite), water and an organic reaction medium (e.g. an alcohol such as isopropanol). The reduction system is then neutralised (e.g. to a pH of 6 to 8.5) with an organic base such as a secondary or tertiary amine (e.g. triethylamine) and reacted with the steroid. When the catalyst system is preformed by heating at reflux, e.g. for 16 to 72 hours, the reduction can be accomplished for example in 2–3 hours at reflux; longer times may be necessary at room temperature.

5β-steroids may be prepared by hydride reduction of the corresponding 3-oxo compound for example with sodium borohydride using an alcohol (e.g. ethanol) or pyridine as solvent.

5. Conversion of a N,N-disubstituted 11α-amine into a N-mono-substituted compound.

Compounds of formula (I) can be prepared from corresponding 11α-tertiary amino compounds by replacement of one of the groups by a hydrogen atom, e.g. by dealkylation using for example sodium nitrite followed by catalytic hydrogenolysis.

Thus, in particular, the compounds may be prepared by deprotection of a corresponding 11α-(protected amino) compound having a substituent $R^1$ in addition to the protecting group, which may be, for example an acyl group such as a trichloroethoxycarbonyl, trifluoroacetyl or formyl group or a silyl group e.g. a trimethylsilyl group. An acyl group may be removed by hydrolysis e.g. with acid or alkali. The trichloroethoxycarbonyl group may also be removed by reduction with, for example, zinc and acetic acid. Alternatively an arylmethyl protecting group such as a benzyl group may be removed by catalytic hydrogenation to produce the unprotected 11α-amino compound. A silyl group may be removed by e.g. solvolysis, with water (optionally containing acid or base) or an alcohol, or by treatment with an ionic fluoride such as tetrabutylammonium fluoride.

This method may also be used to prepare compounds of formula (II) in which $R^4$ is hydrogen, by deprotection of a corresponding 11α-(protected amino) compound to yield a free 11α-amino group.

6. Esterification of a corresponding 17β-carboxylic acid.

Compounds of formula (I) may be prepared by reacting the corresponding compound of formula (II) in which $R^5$ is hydrogen or a reactive derivative thereof (e.g. an acid halide or anhydride or a salt) with the appropriate alcohol or alkyl or cycloalkyl halide. This reaction is preferably carried out at temperatures of $-20°$ C. to $+110°$ C., as is described for example in our British patent specification No. 1,380,246.

Where an alcohol is used in the esterification reaction, a coupling agent may be employed, for example a carbodiimide such as dicyclohexylcarbodiimide, preferably in the presence of a catalyst such as 4-dimethylaminopyridine.

Alternatively, esterification may be effected using a diazoalkane such as diazomethane.

Compounds of formula (II) having $R^5$=hydrogen can conveniently be formed by oxidising the corresponding 17β-acetyl compound, i.e. a pregnan-20-one, using for example NaOBr in an aqueous inert solvent medium (e.g. aqueous dioxan).

Compounds of formula (II) wherein $R^5$ is a hydrogen atom may also be prepared from their corresponding esters having 17β-ester groups other than the group $R^3$ as defined above, for example by hydrolysis under acidic or basic conditions. Examples of suitable acids for such hydrolyses include mineral acids such as hydrochloric acid; examples of suitable bases include alkali metal hydroxides and carbonates, such as sodium or potassium hydroxides or carbonates.

When using certain of the above reagents, for example alkyl halides, it may be necessary to protect the 11α-amino group, for example as a trichloroethoxycarbonyl derivative.

7. Reduction of a corresponding $\Delta^{16}$-compound. The reduction may be effected by hydrogenation in the presence of a catalyst (e.g. a palladium catalyst) in a suitable solvent (e.g. an alcohol, ether or ester). The reaction may be effected conveniently at or about room temperature and atmospheric pressure in the presence of a tertiary base, e.g. triethylamine, and/or an acid, e.g. acetic acid.

The starting materials may be prepared by reaction of the corresponding 17-oxo compound with aqueous hydrogen cyanide to produce the 17-cyanohydrin which may be dehydrated to produce the $\Delta^{16}$-17β-cyano compound. This yields on hydrolysis the $\Delta^{16}$-17β-carboxylic acid and on alkylation, the corresponding $\Delta^{16}$-17β-ester.

8. Compounds of formula (I) may also be prepared by transesterification i.e. by reaction of a corresponding compound having a 17β-ester group other than the desired group $R^3$ with an alcohol of formula $R^3OH$ in the presence of an acid or base catalyst at any temperature from room temperature to reflux, conveniently from 50° to 100° C., so as to produce a compound of formula (I) having a different 17β-ester group from the starting material; normally an excess of alcohol is used. Examples of suitable acid catalysts include mineral acids e.g. sulphuric and hydrochloric, and examples of suitable base catalysts include alkali metal hydroxides and carbonates, e.g. sodium or potassium hydroxides or carbonates.

9. Inversion of a corresponding 3β-hydroxy compound.

The compounds of formula (I) may be prepared from corresponding 3β-hydroxy compounds by introducing a readily displaceable 3β-group such as a hydrocarbylsulphonyloxy (e.g. a p-toluenesulphonyloxy or mesyloxy) group, the 3β-group being displaced by hydrolysis (e.g. in acid conditions) to give the desired 3α-hydroxy group.

Alternatively, the 3β-alcohol may be treated with diethyl azodicarboxylate in the presence of an acid such as formic or benzoic acid and a phosphine such as triphenyl phosphine and the resulting 3α-protected hydroxy compound may be deprotected as described in 10. below.

10. Deprotection of a corresponding compound having a protected 3α-hydroxy group.

Compounds corresponding to compounds of formula (I) but containing protected (e.g. esterified or etherified) 3α-hydroxy groups may be formed where a 3α-hydroxy group is deliberately protected or where esterification or etherification of a 3α-hydroxy group takes place under the same conditions as a reaction elsewhere in the molecule.

An ester (e.g. alkanoyloxy) group may be hydrolysed to give the desired 3α-hydroxy compound under mild acidic or basic conditions. Weakly basic conditions are generally most convenient (using for example an alkali metal bicarbonate in aqueous methanol at any suitable temperature up to reflux). Dilute mineral acids (e.g. perchloric acid in aqueous methanol) may also be used.

An ether (e.g. tetrahydropyranyl ether) protecting group may be removed by treatment with an aqueous acid and a nitro-oxy protecting group by reduction, for example using zinc and acetic acid.

12. Acid addition salts may be prepared by reaction of the free base with a suitable acid.

The methods indicated above for preparing the compounds of the invention can be used as the last main step in a preparative sequence. The same general methods can be used for the introduction of the desired groups at an intermediate stage in the stepwise formation of the required compound, and it will be appreciated that these general methods can be combined in many different ways in such multi-stage processes, as will be apparent from the Examples below. The sequence of the reactions in multi-stage processes should of course be chosen so that the reaction conditions used do not affect groups in the molecule which are desired in the final product.

The D-homo analogues of the compounds of the invention having a group $-CO_2R^3$ at the 17aβ-position may be prepared by essentially similar methods, using appropriate starting materials of the required structure.

Unless otherwise stated, the methods given above for the preparation of compounds of formula (I) are also applicable for the preparation of the compounds of formula (II). Base salts of the compounds of formula (II) may be prepared by the reaction of the free acid with a suitable base. For example, alkali metal salts may be prepared by reaction with an alkali metal hydroxide, carbonate, bicarbonate or 2-ethylhexanoate.

The compounds of formula (I) and their physiologically acceptable acid addition salts may be formulated for administration in any convenient way, and the invention therefore includes within its scope pharmaceutical compositions comprising at least one compound of formula (I) or a physiologically acceptable salt thereof adapted for use in human or veterinary medicine. Such compositions may be presented for use in conventional manner in admixture with one or more pharmaceutical carriers or excipients.

The compounds of formula (I) and their physiologically acceptable acid addition salts may for example be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth, mucilage of starch or polyvinylpyrollidone; fillers, for example lactose, sugar, maize-starch, calcium phosphate or sorbitol; lubricants, for example magnesium stearate, talc, polyethylene glycol or silica; disintegrants, for example potato starch or sodium starch glycollate; or acceptable wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example sorbitol syrup, methyl cellulose, glucose/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; and preservatives, for example methyl or propyl p-hydroxybenzoates or sorbic acid. The compounds or their salts may also be formulated as suppositories, e.g. containing conventional suppository bases such as cocoa butter or other glycerides.

The compounds of formula (I) and their physiologically acceptable acid addition salts may also be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

When the compositions comprise dosage units, each unit will preferably contain at least 5 mg, more preferably at least 10 mg of the active ingredient, advantageously 25–500 mg. The daily dosage as employed for adult human treatment will preferably range from 25–2500 mg preferably 50–1000 mg depending on the route and frequency of administration. The compounds may be given in divided doses, for example 1–4 times per day.

The compounds of formula (I) and their physiologically acceptable acid addition salts may be administered in combination with other therapeutic agents.

The following Examples illustrate the invention.

Melting points were determined in capillaries and are corrected. Optical rotations were determined at room temperature on 1% solutions in chloroform.

Preparative t.l.c. and column chromatography were carried out on silica.

Petrol refers to petroleum ether b.p. 60°–80° C.

Solutions were dried using anhydrous sodium sulphate.

IR spectra were determined in bromoform and refer to the carbonyl stretching frequency of the 17$\beta$-carboxylic acid ester group.

Chloroiridic acid reagent was prepared by refluxing a mixture of chloroiridic acid (50 mg), isopropanol (94 ml), water (6 ml) and trimethylphosphite for 24 hours and adjusting to pH7 by the addition of triethylamine immediately prior to use.

Jones reagent was prepared from chromium trioxide (26.8 g) and concentrated sulphuric acid (23.0 ml) diluted to 100 ml with water.

The following abreviations are used in the Tables:
A=acetonitrile, Ch=chloroform, M=methanol,
I=isopropanol, Am=0.88 ammonia, E=ethanol,
D=diethylether, Ea=ethyl acetate and Pe=petrol.

Intermediate 1

11$\alpha$-Amino-5$\alpha$-pregn-2-en-20-one

A solution of 20,20-ethylenedioxy-5$\alpha$-pregn-2-en-11-one 11-oxime (9.36 g) in propan-1-ol (215 ml) was heated at reflux and sodium (8 g) was added over 2 hours. When all the sodium was consumed the propan-1-ol was removed by distillation. The residue was extracted with ether (x 3) and these extracts were extracted with 2 M-HCl solution (x 3). The extracts were washed with ether and brought to pH 9 with 0.88 NH$_3$ solution. The mixture was extracted with ether (x 2) and the extracts were washed with water, dried and evaporated to leave a solid (8.77 g) which was crystallised from ethyl acetate/petrol to give the title compound (6.15 g) in two crops. A portion was recrystallised from ethyl acetate/petrol, m.p. 127°–129° C., $[\alpha]_D+121°$.

Intermediate 2

11$\alpha$-(2,2,2-Trichloroethoxycarbonylamino)-5$\alpha$-pregn-2-en-20-one

A solution of Intermediate 1 (0.331 g) in pyridine (3 ml) was treated with 2,2,2-trichloroethyl chloroformate (0.3 ml) and the mixture was stirred at room temperature. After 0.5 hour, the reaction mixture was diluted with water (30 ml) and extracted with ether (x 3). The combined ethereal extracts were washed with water (x 3), dried and evaporated to give an oil. Purification by preparative t.l.c. in ethyl acetate:petrol 1:3 gave the title compound as a foam (0.397 g), $[\alpha]_D+56°$.

Intermediate 3

2$\beta$-Ethoxy-11$\alpha$-(2,2,2-trichloroethoxycarbonylamino)-3$\alpha$-(2,2,2-trichloroethoxycarbonyloxy)-5$\alpha$-pregnan-20-one 2,2,2-Trichloroethyl chloroformate (1 ml) was added to a stirred solution of 11$\alpha$-amino-2$\beta$-ethoxy-3$\alpha$-hydroxy-5$\alpha$-pregnan-20-one (2 g) in pyridine (20 ml). After 16 hours complete reaction was not obtained. A further quantity of 2,2,2-trichloroethyl chloroformate (1 ml) was added and after 30 minutes the mixture was diluted with water (30 ml). The mixture was extracted with ether (x 2) and the extracts were washed with 2 M-HCl (x 4) and water (x 2) and dried. Evaporation of the solution left a yellow froth which was purified by column chromatography on silica eluted with ethyl acetate:petrol (1:3) to give a solid (2.5 g). A portion was crystallised from ether/petrol to give the title compound m.p. 147°–149° C., $[\alpha]_D+48°$.

Intermediate 4

11$\alpha$-(2,2,2-Trichloroethoxycarbonylamino)-5$\alpha$-androst-2-ene-17$\beta$-carboxylic acid Bromine (0.61 ml) was added to a solution of sodium hydroxide (1.44 g) in water (10.8 ml) keeping the temperature at $-10°$ C. Dioxan (5.4 ml) was added and the resultant mixture was added to a stirred solution of Intermediate 2 (1.47 g) in dioxan (25.5 ml) and water (8.1 ml) at 10° C. After 4 hours at 10° C. sodium sulphite (0.45 g) was added and the mixture was stirred for 0.25 hour. The reaction mixture was filtered and the filtrate was brought to pH 2 with concentrated HCl solution. The suspension was extracted with chloroform ($\times$3). The extract was washed with water, dried and evaporated to leave a froth (1.3 g) which was purified by preparative t.l.c. in CHCl$_3$:MeOH (9:1) to give the title compound (1.08 g), $[\alpha]_D+24°$.

Intermediate 5

2$\beta$-Ethoxy-3$\alpha$-hydroxy-11$\alpha$-(2,2,2-trichloroethoxycarbonylamino)-5$\alpha$-androstane-17$\beta$-carboxylic acid Following the method used for Intermediate 4 the title compound (680 mg; $[\alpha]_D+13°$) was prepared from Intermediate 3 (2.5 g) using bromine (0.6 ml) and a solution of NaOH (1.75 g) in water (13 ml).

Intermediate 6

Methyl 2$\beta$-ethoxy-3$\alpha$-hydroxy-11$\alpha$-(2,2,2-trichloroethoxycarbonylamino)-5$\alpha$-androstane-17$\beta$-carboxylate Potassium carbonate (1.15 g) and methyl iodide (0.8 ml) were added to a solution of Intermediate 5 (1.4 g) in DMF (25 ml) at 0° C. The mixture was stirred for 2 h when the solid was removed by filtration. The filtrate was diluted with water (50 ml) and extracted with ethyl acetate (x2). The extract was washed with brine (x2) and water and dried. Evaporation give an oil (1.586 g) which was purified by column chromoatgraphy eluted with ethyl acetate/petrol (1:2) to give the title compound (1.211 g), $[\alpha]_D+17.5°$.

Intermediate 7 to 11

Table 1 summarises the preparation of 17$\beta$-esters using the general method described for Intermediate 6.

Intermediate 7 is methyl 3$\alpha$-hydroxy-11$\alpha$(2,2,2-trichloroethoxycarbonylamino)-5$\beta$-androstane-17$\beta$-carboxylate.

Intermediates 8 to 10 are esters of 2$\beta$-ethoxy-3$\alpha$-hydroxy-11$\alpha$-(2,2,2-trichloroethoxycarbonylamino)-5$\alpha$-androstane-17$\beta$-carboxylic acid.

Intermediate 11 is ethyl 11$\alpha$-(2,2,2-trichloroethoxycarbonylamino)-5$\alpha$-androst-2-ene-17$\beta$-carboxylate.

TABLE 1

| Inter. No. | Starting Material Inter. No. | Wt (g) | Alkyl Halide reagent | Vol (ml) | K$_2$CO$_3$ (g) | Reaction Time (h) | Yield (g) | $[\alpha]_D$ |
| --- | --- | --- | --- | --- | --- | --- | --- | --- |
| 7 | 23 | 21.9 | Iodomethane | 13.75 | 19.6 | 1.5 | 23.07 | +30° |
| 8 | 5 | 1.5 | 1-Iodopropane | 1.2 | 1.3 | 17.0 | 1.54 | |
| 9 | 5 | 1.5 | 1-Bromo-3-methylbutane | 1.5 | 1.3 | 19.0 | 1.6 | |
| 10 | 5 | 0.62 | Iodoethane | 0.5 | 0.5 | 1.75 | 0.35 | +12.5° |
| 11 | 4 | 0.87 | Iodoethane | 1.4 | 0.73 | 1.5 | 0.7 | +25° |

Intermediate 12

Methyl 11$\alpha$-(2,2,2-trichloroethoxycarbonylamino)-5$\alpha$-androst-2-ene-17$\beta$-carboxylate A solution of Intermediate 4 (1.064 g) in DMF (24 ml) was stirred at 0° C. with K$_2$CO$_3$ (0.893 g) and methyl iodide (0.67 ml) for 1.5 hour. The mixture was filtered and the filtrate was diluted with water (50 ml) and extracted with ethyl acetate (x3). The extract was washed with brine and water, dried and evaporated to leave a froth (0.798 g) which was purified by preparative t.l.c. using EtOAc:Petrol (1:3) to give the title compound (0.621 g) as a froth, $[\alpha]_D+26.5°$.

Intermediate 13

Methyl 2$\alpha$,3$\alpha$-epoxy-11$\alpha$-(2,2,2-trichloroethoxycarbonylamino)-5$\alpha$-androstane-17$\beta$-carboxylate A solution of Intermediate 12 (12.372 g) in dichloromethane (200 ml) was treated with m-chloroperoxybenzoic acid (6.56 g). After 1 h the reaction mixture was washed with NaHSO$_3$ solution, NaHCO$_3$ solution and water. The aqueous washes were extracted with dichloromethane and the combined extract was washed with water, dried and evaporated to leave a froth (11.531 g). A portion was purified by preparative t.l.c. in EtOAc/Petrol (1:3) to give the title compound, $[\alpha]_D+21°$.

Intermediate 14

Ethyl 2$\alpha$,3$\alpha$-epoxy-11$\alpha$-(2,2,2-trichloroethoxcarbonylamino)-5$\alpha$-androstane-17$\beta$-carboxylate Following the method used for Intermediate 13 the title compound (544 mg; $[\alpha]_D+16°$) was prepared from Intermediate 11 (620 mg) using m-chloroperoxybenzoic acid (319 mg). Purification was effected by preparative t.l.c. using CHCl$_3$:MeOH (19:1).

Intermediate 15

Cyclohexyl 2$\beta$-ethoxy-3$\alpha$-hydroxy-11$\alpha$-(2,2,2-trichloroethoxycarbonylamino)-5$\alpha$-androstane-17$\beta$-carboxylate A solution of Intermediate 5 (2.2 g) in ether (20 ml) was stirred with cyclohexanol (2.1 ml), dicyclohexylcarbodiimide (0.907 g) and 4-dimethylaminopyridine (0.056 g) for 18 h. Ether (100 ml) was added and the mixture was filtered. The filtrate was washed with 2M-HCl solution (x2), NaHCO$_3$ solution and brine, dried and evaporated to leave a froth (2.902 g).

Intermediate 16

Methyl 11$\alpha$-amino-2$\alpha$,3$\alpha$-epoxy-5$\alpha$-androstane-17$\beta$-carboxylate Toluene-4-sulphonic acid (570 mg) was added to a solution of methyl 11$\alpha$-amino-5$\alpha$-androst-2-ene-17$\beta$-carboxylate (1.0 g) in 1,2-dichloroethane (25 ml). After 0.5 h m-chloroperoxybenzoic acid (810 mg) was added and the mixture was left for a further 2 h. The mixture was washed with NaHSO$_3$ solution, 5% NaHCO$_3$ solution and water. The aqueous phases were extracted with dichloromethane and the combined organic phase was dried and evaporated to leave a foam which was purified by preparative t.l.c. in MeOH: 0.88 NH$_3$ (50:1) to give the title compound (369 mg) as a foam $[\alpha]_D+44°$, $\nu_{max}$ 1722 cm$^{-1}$.

Intermediate 17

Methyl 11$\alpha$-cyclohexylamino-2$\alpha$,3$\alpha$-epoxy-5$\alpha$-androstane-17$\beta$-carboxylate Cyclohexanone (0.3 ml) and sodium cyanoborohydride (300 mg) were added to a solution of Intermediate 16 (300 mg) in ethanol (8 ml) and the mixture was left for 24 h. 5% NaHCO$_3$ solution was added and the mixture was extracted with ether (x3). The extract was washed with water, dried and evaporated to leave a foam which was purified by column chromatography and preparative t.l.c. to give the title compound (80 mg) as a foam [α]$_D$ −2°.

Intermediate 18

11α-(2,2,2-trichloroethoxycarbonylamino)-3α-(2,2,2-trichloroethoxycarbonyloxy)-5α-pregnan-20-one A solution of 11α-amino-3α-hydroxy-5α-pregnan-20-one (19.5 g) in dichloromethane (250 ml) and pyridine (26.5 ml) was cooled in an ice-bath during the addition of 2,2,2-trichloroethyl chloroformate (36 ml). On complete addition, water was carefully added and when no further reaction occurred the mixture was washed with 2M-HCl solution (x2) and water. The solution was dried and evaporated to leave an oil (24.6 g) which was treated with ether to give the title compound (14.1 g) as a solid.

Intermediate 19

3α-Hydroxy-11α-(2,2,2-trichloroethoxycarbonylamino)-5-α-androstane-17β-carboxylic acid Following the method used for Intermediate 4 the title compound was prepared from Intermediate 18 (15.5 g) using bromine (3.85 ml) and a solution of NaOH (11 g) in water (85 ml). Purification was effected by column chromatography eluted with EtOAc/petrol (1:1) to give the title compound (4.73 g). A portion was crystallised from ether/petrol, m.p. dec. 100° C., [α]$_D$+19°.

Intermediate 20

Methyl 3α-hydroxy-11α-(2,2,2-trichloroethoxycarbonylamino)-5α-androstane-17β-carboxylate A solution of Intermediate 19 (4 g) in DMF (80 ml) was stirred with K$_2$CO$_3$ (3.7 g) at 0° C. Methyl iodide (2.6 ml) was added and the mixture was stirred for 2 h. Water (300 ml) was added and the mixture was extracted with ether (x3). The extract was washed with water, dried and evaporated to leave a froth which was purified by column chromatography eluted with EtOAc/petrol (1:2) and crystallised from ether to give the title compound (2.45 g), m.p. 167°–170° C., [α]$_D$+25°.

Intermediate 21

Methyl 3α-hydroxy-2β-methoxy-11α-(2,2,2-trichloroethoxycarbonylamino)-5α-androstane-17β-carboxylate Boron trifluoride diethyl etherate (11.3 ml) was added to a solution of Intermediate 13 (5.266 g) in methanol (60 ml) and the mixture was stirred at room temperature for 1 h. The mixture was diluted with 5% NaHCO$_3$ solution and extracted with ethyl acetate (x3). The extract was washed with water, dried and evaporated to leave a froth. A portion (193 mg) was purified by preparative t.l.c. using ethyl acetate/petrol (1:1) to give the title compound (144 mg) as a froth, [α]$_D$+23°, ν$_{max}$ 1722 cm$^{-1}$.

Intermediate 22

11α-(2,2,2-Trichloroethoxycarbonylamino)-3α-[2,2,2-trichloroethoxycarbonyloxy]-5β-pregnan-20-one Pyridine (39 ml) and 2,2,2-trichloroethyl chloroformate (53 ml) were added to an ice-cooled solution of 11α-amino-3α-hydroxy-5β-pregnan-20-one (26.54 g) in dichloromethane (350 ml). After 2 h water (400 ml) was added and the organic phase was separated and evaporated to leave a brown oil which crystallised on trituration with ether/petrol to give the title compound (47.86 g), m.p. 174°–176° C., [α]$_D$+60°.

Intermediate 23

3α-Hydroxy-11α-(2,2,2-trichloroethoxycarbonylamino)-5β-androstane-17β-carboxylic acid Following the method used for Intermediate 4, bromine (12.5 ml) and a solution of sodium hydroxide (35.1 g) in water (270 ml) was used to convert Intermediate 22 (47 g) into the corresponding 17β-carboxylic acid which was then taken up in dioxan. 2M-NaOH solution was added to give a pH 11 and the mixture was stirred for 3 h. The mixture was brought to pH 2 with concentrated HCl solution and diluted with water. The precipitate was extracted with chloroform (x2) and the extract was washed with water, dried and evaporated to leave an oil which crystallised from ether/petrol to give the title compound (22.5 g), m.p. 250°–251° C., [α]$_D$+34°.

Intermediates 24–28

Table 2 summarises the preparation of 2β-substituted compounds from the corresponding 2α,3α-epoxide using the general method described for Intermediate 21.

Intermediate 24 is ethyl 2β-butoxy-3α-hydroxy-11α-(2,2,2-trichloroethoxycarbonylamino)-5α-androstane-17β-carboxylate.

Intermediates 25–28 are 2β-alkoxy analogues of Intermediate 21.

TABLE 2

| | Starting Material | | Alcohol | | BF$_3$.Et$_2$O | Reaction Time | Yield | |
|---|---|---|---|---|---|---|---|---|
| Inter No. | Inter No. | wt (g) | reagent | Vol (ml) | (ml) | (h) | (g) | [α]$_D$ |
| 24 | 14 | 0.46 | Butan-1-ol | 5.2 | 1.0 | 1 | 0.38 | +11° |
| 25 | 13 | 3.17 | Butan-1-ol | 36.0 | 6.83 | 1 | 3.46 | +15° |
| 26 | 13 | 3.89 | Pentan-1-ol | 50.0 | 8.8 | 24 | 3.40 | +14° |
| 27 | 13 | 4.21 | Hexan-1-ol | 50.0 | 10.0 | 20 | 5.33 | +9° |
| 28 | 13 | 5.22 | Propan-1-ol | 59.0 | 11.2 | 1 | — | +20° |

Intermediate 29

11α-(2,2,2-Trichloroethoxycarbonylamino)-3β-(2,2,2-trichloroethoxycarbonyloxy)-5α-pregnan-20-one Pyridine (12 ml) and 2,2,2-trichloroethyl chloroformate (40 ml) were added to a cooled, stirred solution of 11α-amino-3β-hydroxy-5α-pregnan-20-one (24 g) in dichloromethane (300 ml). After 2 h water (300 ml) was added and the organic phase was separated and the solvent removed by evaporation to leave an oil which was purified by column chromatography eluted with ethyl acetate/petrol (1:4) and (1:2) to give the title compound (27.27 g), [α]$_D$+40°.

Intermediate 30

3β-Hydroxy-11α-(2,2,2-trichloroethoxycarbonylamino)-5α-androstane-17β-carboxylic acid Following the method used for Intermediate 4 the title compound (18.17 g; m.p. 212°–220° C.; [α]$_D$+16°) was prepared from Intermediate 29 (27 g) using bromine (7.2 ml) and a solution of NaOH (20 g) in water (155 ml). The product was crystallised from ether/petrol.

Intermediate 31

Methyl 3β-hydroxy-11α-(2,2,2-trichloroethoxycarbonylamino)-5α-androstane-17β-carboxylate Potassium carbonate (16 g) and methyl iodide (11.2 ml) were added to a stirred solution of Intermediate 30 (17.8 g) in DMF (325 ml) at 0° C. After 1.75 h the mixture was diluted with water (1.5 l) and the precipitate was extracted with ethyl acetate (x2). The extract was washed with brine (x2), dried and evaporated to leave an oil which on evaporation from ether gave the title compound (15.45 g) $[\alpha]_D + 15°$.

Intermediate 32

Methyl 11α-amino-3β-hydroxy-5α-androstane-17β-carboxylate

Zinc powder (36 g) was added to a stirred solution of Intermediate 31 (15 g) in glacial acetic acid (400 ml). The mixture was stirred for 20 h and the zinc was removed by filtration and washed with water. The filtrate was reduced in bulk in vacuo and the residue was brought to pH 10 with 0.88 NH$_3$ solution. The oil was extracted with ethyl acetate (x2) and the extract was washed with brine (x2), dried and evaporated to leave an oil (7.93 g). A sample (400 mg) was purified by preparative t.l.c. to give the title compound as a froth $[\alpha]_D + 29°$.

Intermediate 33

Methyl 11α-cyclohexylamino-3β-hydroxy-5α-androstane-17β-carboxylate

Sodium cyanoborohydride (7.5 g) and cyclohexanone (12 ml) were added to a stirred solution of Intermediate 32 (7.5 g) in ethanol (100 ml). After 60 h the mixture was diluted with 5% NaHCO$_3$ solution (100 ml) and the resultant precipitate was extracted into ether (x2). The extract was shaken with 2M-HCl (x2) and the aqueous phase was washed with ether, brought to pH 9 with 0.88 NH$_3$ solution and extracted with ether (x2). The extract was washed with water (x2), dried and evaporated to a froth whih was purified by column chromatography on silica eluted with CHCl$_3$:MeOH (19:1) to give the title compound (4.411 g) which crystallised from petrol m.p. 82°–84° C., $[\alpha]_D - 1°$.

Intermediate 34

Methyl 11α-cyclohexylamino-3-oxo-5α-androstane-17β-carboxylate

Jones reagent was added dropwise to a stirred solution of methyl 11α-cyclohexylamino-3β-hydroxy-5α-androstane-17β-carboxylate (300 mg) in acetone (40 ml) until the reagent colour was not discharged. Water (200 ml) was added and the mixture was brought to pH 10 with 0.88 NH$_3$ solution. Ether (50 ml) was added and the mixture was filtered. The aqueous phase was separated, extracted with ether (50 ml) and the organic phase was washed with water, dried and evaporated to leave an oil (289 mg) which crystallised from petrol to give the title compound m.p. 93°–94° C., $[\alpha]_D - 12°$.

Intermediate 35

3α-Hydroxy-11-hydroxyimino-5α-androstane-17β-carboxylic acid

Hydroxylamine hydrochloride (4 g) was added to a water cooled solution of sodium hydroxide (50%; 16 ml). This mixture was added to a solution of 3α-hydroxy-11-oxo-5α-androstane-17β-carboxylic acid (1.5 g) in ethanol (70 ml). The mixture was heated at reflux for 24 h, cooled and brought to pH 1 with concentrated HCl solution. Water (800 ml) was added and the precipitate (1.42 g) was collected by filtration, washed with water (2×300 ml) and dried. Crystallisation from ethyl acetate gave the title compound (1 g) m.p. 250°–253° C. (dec) $[\alpha]_D + 124°$ (EtOH C=1%).

Intermediate 36

11α-Cyclohexylamino-2β-ethoxy-3α-hydroxy-5α-pregnan-20-one

A solution of 11α-amino-2β-ethoxy-3α-hydroxy-5α-pregnan-20-one 20-ethylene acetal (2 g) in ethanol (20 ml) was stirred with cyclohexanone (1.5 ml) and sodium cyanoborohydride (2.015 g) for 6 h. 5% NaHCO$_3$ solution (40 ml) was added and the mixture was extracted with ether (x2). The extract was washed with water (x2), dried and evaporated to leave a froth which was dissolved in 2M-HCl solution (50 ml) and ethanol (50 ml). Water (100 ml) was added and the mixture was washed with ether (x2). The wash was extracted with 2M-HCl solution and the combined acid fraction was brought to basic pH with 2M-NaOH solution. The mixture was extracted with ether (x2) and the extract was washed with water (x2), dried and evaporated to leave a froth which was purified by column chromatography eluted with CHCl$_3$:MeOH (9:1) to give the title compound (1.235 g), $[\alpha]_D + 39°$. $\nu_{max}$ 1695 cm$^{-1}$.

Intermediate 37

Methyl 2β-acetoxy-3α-hydroxy-11α-(2,2,2-trichloroethoxycarbonylamino)-5α-androstane-17β-carboxylate Intermediate 13 (20.5 g) in glacial acetic acid (100 ml) was heated on a steam bath for 3.25 h. The reaction mixture was allowed to cool, concentrated by evaporation and then diluted with 0.88 NH$_3$ solution to pH 9.0. This was extracted with ethyl acetate (3x). The extracts were washed with water (1x), dried and evaporated to a foam (23.8 g). A small sample was purified by preparative t.l.c. in EtOAc/Petrol (1:1) and crystallised from ether to give the title compound (220 mg), m.p. 200°–201° C., $[\alpha]_D + 26.1°$.

Intermediate 38

2β-Ethoxy-3α-hydroxy-11α-(3-methylbutylamino)-5α-pregnan-20-one

11α-amino-2β-ethoxy-3α-hydroxy-5α-pregnan-20-one 20-ethylene acetal (20 g) in ethanol (200 ml) was stirred with K$_2$CO$_3$ (25 g), NaI (1 g) and 1-bromo-3-methylbutane (50 ml) and the mixture was heated at reflux for 24 h. The excess K$_2$CO$_3$ was removed by filtration and washed with ethanol. The filtrate and washings were acidified with 2M-HCl to pH 2, washed with ether and the ether wash in turn washed with M-HCl and water (x3). The aqueous layers were brought to pH 10 with 2M-NaOH and the resulting suspension was extracted with ether (x2). The ether layers were combined, washed with water (x2), dried and evaporated to leave a froth (18.96 g), which was purified by column chromatography eluted with CHCl$_3$/MeOH (19:1) and crystallised from acetonitrile to give the title compound (9.211 g), m.p. 110.5°–112° C., $[\alpha]_D + 56°$.

EXAMPLES—SECTION A

EXAMPLE 1

Methyl 11α-amino-2β-ethoxy-3α-hydroxy-5α-androstane-17β-carboxylate

Zinc powder (2.4 g) was added to a stirred solution of Intermediate 6 (1.1 g) in glacial acetic acid (25 ml) and the mixture was stirred for 6 hours. The zinc was removed by filtration and washed with water. The aqueous filtrate was washed with ether (x2) then brought to pH 10 with 2M-NaOH solution. The mixture was extracted with ether (x2) and the extract was washed with water (x2), dried and evaporated to leave an oil (580 mg) which was purified by preparative t.l.c. using methanol to give the title compound (180 mg), $[\alpha]_D +46°$. $\nu_{max}$ 1725 cm$^{-1}$.

EXAMPLE 2

Methyl 11α-amino-3α-hydroxy-5α-androstane-17β-carboxylate

A solution of Intermediate 20 (2.4 g) in glacial acetic acid (25 ml) was stirred with zinc (2.5 g) for 4 hours. The zinc was removed by filtration and washed with water (50 ml) and ether (50 ml). The filtrate and washings were brought to pH 10 with 0.88 NH$_3$ solution and extracted with ether (x4). The extract was washed with 6. Propyl 11α-amino-2β-ethoxy-3α-hydroxy-5α-androstane-17β-carboxylate,
7. Ethyl 11α-amino-2β-butoxy-3α-hydroxy-5α-androstane-17β-carboxylate,
8. Methyl 11α-amino-2β-butoxy-3α-hydroxy-5α-androstane-17β-carboxylate
9. Methyl 11α-amino-3α-hydroxy-2β-pentyloxy-5α-androstane-17β-carboxylate,
10. Methyl 11α-amino-2β-hexyloxy-3α-hydroxy-5α-androstane-17β-carboxylate,
11. Cyclohexyl 11α-amino-2β-ethoxy-3α-hydroxy-5α-androstane-17β-carboxylate,
12. Methyl 11α-amino-3α-hydroxy-2β-propoxy-5α-androstane-17β-carboxylate,
13. Methyl 11α-amino-3α-hydroxy-5β-androstane-17β- carboxylate,
14. Methyl 2β-acetoxy-11α-amino-3α-hydroxy-5α-androstane-17β-carboxylate.

TABLE 3

| Example No. | Starting Material Inter. No. | wt (g) | Zinc (g) | Acetic Acid (ml) | Reaction Time (h) | Purification System | Yield (g) | $[\alpha]_D$ | M.P./ $\nu_{max}$ |
|---|---|---|---|---|---|---|---|---|---|
| 4[2] | 10 | 1.225 | 2.4 | 25 | 6 | P—M | 0.391 | +39.5° | 1720 cm$^{-1}$ |
| 5[1] | 9 | 1.61 | 3.0 | 25 | 7.5 | X—A | 0.573 | +36° | 122–124° |
| 6 | 8 | 1.54 | 3.0 | 35 | 3.5 | P—Ch:M (9:1); X—A | 0.341 | +40° | 130–135° |
| 7[1] | 24 | 3.305 | 3.3 | 10 | 3 | P—Ch:M (5:1) and I:Am (40:1) | 0.428 | +31° | 1715 cm$^{-1}$ |
| 8 | 25 | 3.04 | 3.0 | 10 | 3 | P—I:Am (40:1) | 1.8 | +35° | 1725 cm$^{-1}$ |
| 9 | 26 | 3.106 | 3.1 | 20 | 18 | P—I:Am (40:1) | 1.8 | +33° | 1730 cm$^{-1}$ |
| 10 | 27 | 4.923 | 4.9 | 25 | 18 | P—M:Am (50:1) | 3.2 | +33° | 1724 cm$^{-1}$ |
| 11[1] | 15 | 2.902 | 3.9 | 50 | 7 | C—E:M (3:1) | 0.321 | +33° | 1712 cm$^{-1}$ |
| 12 | 28 | 5.247 | 5.2 | 15 | 1 | P—I:Am (40:1) | 0.389[3] | +42° | 1719 cm$^{-1}$ |
| 13[1] | 7 | 22 | 52.5 | 600 | 20 | — | 13.56 | +36° | — |
| 14 | 37 | 22.85 | 22 | 100 | 22 | X—D | 4.534 | +49.9° | 158–160° |

[1]Ethyl acetate used in place of ether for extraction.
[2]The ethereal washes were also extracted and the extracts combined.
[3]Only a portion of the product was purified.

water, dried and evaporated to leave a solid (1.65 g). A portion was crystallised from ether to give the title compound, m.p. 113°–116° C., $[\alpha]_D +38°$.

EXAMPLE 3

Methyl 11α-amino-3α-hydroxy-2β-methoxy-5α-androstane-17β-carboxylate

Zinc powder (4.9 g) was added to a stirred solution of Intermediate 21 (4.874 g) in glacial acetic acid (15 ml) and the mixture was stirred for 1 h. The zinc was removed by filtration and washed with water. The filtrate and washings were brought to pH 10 with 0.88 NH$_3$ solution and extracted with ether (x3). The extract was washed with water, dried and evaporated to leave a solid which was crystallised from ethyl acetate to give the title compound (1.716 g), m.p. 177°–184° C., $[\alpha]_D +53°$.

EXAMPLES 4–16

Table 3 summarises the preparation of 11α-amino compounds from the corresponding 11α-(2,2,2-trichloroethoxycarbonylamino)-compunds using the general method described in Example 1–3.

Purification was effected by preparative t.l.c. (P), column chromatography (C) or cyrstallisation (X).

The compounds prepared were as follows:
4. Ethyl 11α-amino-B 2β-ethoxy-3α-hydroxy-5α-androstane-17β-carboxylate,
3-Methylbutyl 11α-amino-2β-ethoxy-3α-hydroxy-5α-androstane-17β-carboxylate,

EXAMPLE 15

2β-Ethoxy-3α-hydroxy-11α-(3-methylbutylamino)-5α-androstane-17β-carboxylic acid

A solution of the product of Example B1 (500 mg) in dioxan (10 ml) was heated at 100° C. with concentrated hydrochloric acid (1.5 ml) and water (5 ml) for 5 days. The cooled mixture was brought to pH 11 with 50% aqueous sodium hydroxide solution and extracted with ether (x3). The extract was washed with water, dried and evaporated to leave the title compound as a solid, $[\alpha]_D +54°$, $\nu_{max}$ 1635 cm$^{-1}$, 1550 cm$^{-1}$.

A sample (20 mg) of this product was dissolved in methanol (1 ml) and the solution was heated at reflux with concentrated sulphuric acid (1 drop) for 4 hours. t.l.c. of the reaction mixture showed formation of methyl 2β-ethoxy-3α-hydroxy-11α-(3-methylbutylamino)-5α-androstane-17β-carboxylate.

EXAMPLE 16

Methyl 11α-amino-3α-hydroxy-5α-androstane-17β-carboxylate

Sodium (1 g) was added to a refluxing solution of Intermediate 35 (0.3 g) in propan-1-ol (20 ml). When all the sodium had been consumed water (10 ml) was added. The mixture was evaporated and the residue was dissolved in 2M-HCL (20 ml). The solution was evaporated to dryness and azetroped with benzene (x3). The resultant oil was dissolved in methanol (30 ml) and the solution was heated at reflux with concentrated H$_2$SO$_4$ (0.5 ml) for 3 h. The cooled mixture was brought to basic pH with 0.88 NH$_3$ solution and diluted with water (100 ml). The precipitate was extracted with ether (x2) and the extract was washed with water, dried and evaporated to leave a froth which was dissolved in ether (50 ml). The solution was extracted with 2M-HCl solution (x2) and water. The aqueous extract was brought to pH 10 with 0.88 NH₃ solution and the precipitate was extracted with ether (x3). The extract was washed with water, dried and evaporated to leave the title compound (226 mg) as a froth $[\alpha]_D+35°$.

EXAMPLE 17

2β-Ethoxy-3α-hydroxy-11α-(3-methylbutylamino)-5α-androstane-17β-carboxylic acid

Bromine (0.4 ml) was added to a solution of sodium hydroxide (1.24 g) in water (16 ml) at 0° C. Dioxan (6 ml) was added and the mixture was added to a solution of Intermediate 38 (1.14 g) in dioxan (50 ml) and water (16 ml) at 10° C. After 6 h sodium metabisulphite (10 g) was added and the mixture was stirred for 0.5 h. Concentrated HCl solution was added to bring the pH to 1 and the mixture was evaporated to dryness. The solid was leached with ether and ethyl acetate and the solutions evaporated to leave the title compound as a solid (1.31 g).

EXAMPLES 18–26

Table 4 summarises the preparation of the hydrochloride salts of the 11α-amines.

A solution of hydrochloric acid in water was added to the base or a suspension of the base in any additional water and the mixture was stirred or shaken until either a clear solution was obtained or no more base dissolved. The mixture was made up to the appropriate weight or volume with water and filtered and any undissolved base was collected, dried and weighed to determine the solution concentration. The pH was measured.

(x2). The total aqueous phase was brought to pH 10 with 2M-NaOH solution and extracted with ether (x2). The extract was washed with water (x2) dried and evaporated to leave an oil which was purified by crystallisation from acetonitrile to give the title compound (914 mg), m.p. 122°–124° C., $[\alpha]_D+22°$.

EXAMPLE 2

Methyl 3α-hydroxy-2β-methoxy-11α-(3-methylbutylamino)-5α-androstane-17β-carboxylate 1-Bromo-3-methylbutane (9.54 ml), potassium carbonate (2.94 g) and sodium iodide (0.111 g) were added to a stirred solution of the product of Example A3 (2.408 g) in ethanol (43 ml) and the mixture was heated at reflux for 22 h. The cooled mixture was diluted with water and extracted with ethyl acetate (x3) The extract was washed with water, dried and evaporated to a froth which was purified by preparative t.l.c. using CHCl₃:MeOH (19:1) to give the title compound (1.24 g), $[\alpha]_D+22°$, $\nu_{max}$ 1724 cm⁻¹.

EXAMPLES 3–10

Table 5 summarises the preparation of 11α-alkylamino compounds from the corresponding 11α-amines using the general method of Examples 1 and 2. Work up was either as in Example 1 (I) or in Example 2 (II).

Purification was effected by preparative t.l.c. (P), column chromatography (C) or crystallisation (X).

In Examples 3–7 and 9 the haloalkane was 1-bromo-3-methylbutane, in Example 8 it was iodopropane and in Example 10 it was 1-iodo-3-methylbutane.

The compounds prepared were as follows:
3. Ethyl 2β-ethoxy-3α-hydroxy-11α-(3-methylbutylamino)-5α-androstane-17β-carboxylate,
4. Methyl 2β-butoxy-3α-hydroxy-11α-(3-methyl-

TABLE 4

| Example No | Example No of free base | Wt (mg) | HCl M | HCl Vol (ml) | Additional Water (ml) | Total Weight or Volume | Solid residue (mg) | pH | Conc'n. (%) |
|---|---|---|---|---|---|---|---|---|---|
| 18 | 1 | 100 | 0.0963 | 2.7 | 5 | 10 ml | — | 2.4 | 1 |
| 19 | 4 | 100 | 0.0963 | 2.55 | 3 | 10 ml | — | 3.1 | 1 |
| 20 | 6 | 100 | 0.0963 | 2.46 | 2 | 10 ml | — | 5.0 | 1 |
| 21 | 5 | 100 | 0.0963 | 2.35 | 3 | 20 ml | — | 3.2 | 0.5 |
| 22 | 7 | 349.8 | 0.0924 | 7.42 | 20 | 30 ml | 10.8 | 6.0 | 1.13 |
| 23 | 8 | 375.6 | 0.0924 | 9.64 | — | 30.02g | — | 2.4 | 1.25 |
| 24 | 9 | 175.7 | 0.0924 | 4.36 | — | 10.04g | — | 2.3 | 1.75 |
| 25 | 10 | 518.3 | 0.0924 | 12.47 | — | 50.05g | 63 | 2.55 | 0.9 |
| 26 | 17 | 100 | 0.0924 | 2.4 | — | 10 ml | — | 2.7 | 1 |

EXAMPLES—SECTION B

EXAMPLE 1

Methyl 2β-ethoxy-3α-hydroxy-11α-(3-methylbutylamino)-5α-androstane-17β-carboxylate Potassium carbonate (2.514 g), sodium iodide (107 mg) and 1-bromo-3-methylbutane (6 ml) were added to a stirred solution of the product of Example A1 (2 g) in ethanol (30 ml) and the mixture was heated at reflux for 24 hours. The reaction was cooled and acidified with 2M-HCl solution and washed with ether. The ethereal wash was extracted with M-HCl solution and water butylamino)-5α-androstane-17β-carboxylate,
5. Methyl 3α-hydroxy-11α-(3-methylbutylamino)-2β-pentyloxy-5α-androstane-17β-carboxylate,
6. Methyl 2β-hexyloxy-3α-hydroxy-11α-(3-methylbutylamino)-5α-androstane-17β-carboxylate,
7. Methyl 3α-hydroxy-11α-(3-methylbutylamino)-5α-androstane-17β-carboxylate,
8. Methyl 2β-ethoxy-3α-hydroxy-11α-propylamino-5α-androstane-17β-carboxylate,
9. Methyl 3α-hydroxy-2β-propoxy-11α-(3-methylbutylamino)-5α-androstane-17β-carboxylate,
10. Methyl 3α-hydroxy-11α-(3-methylbutylamino)-5β-androstane-17β-carboxylate.

TABLE 5

| Ex. No. | Starting Material Ex. No. | wt (g) | Ethanol (ml) | Haloalkane (ml) | K$_2$CO$_3$ (g) | NaI (mg) | Reaction Time (h) | Work up method | Purification System | Yield (g) | $[\alpha]_D$ | MP/ $\nu_{max}$ |
|---|---|---|---|---|---|---|---|---|---|---|---|---|
| 3 | A4 | 2.02 | 30 | 6 | 2.51 | 105 | 24 | I | C—Ch:M (9:1) X—A | 1.0 | +18.5° | 100–102° |
| 4 | A8 | 0.87 | 15 | 3.35 | 1.03 | 39 | 32 | II | P—Ea:Pe (1:1) | 0.39 | +16° | 1722 cm$^{-1}$ |
| 5 | A9 | 0.91 | 16 | 3.5 | 1.03 | 41 | 24 | II | P—Ea:Pe (1:2) | 0.31 | +17° | 1720 cm$^{-1}$ |
| 6 | A10 | 1.78 | 30 | 6.8 | 2.1 | 80 | 22 | II | P—Ea | 0.76 | +14° | — |
| 7 | A2 | 1.6 | 30 | 5 | 2.3 | — | 24 | II[1] | P—Ch:M (9:1) and D | 0.46 | +18° | 1725 cm$^{-1}$ |
| 8 | A1 | 2.5 | 30 | 9 | 3.5 | — | 7.5 | I | P and C— Ch:M (9:1) | 1.36 | +24° | 1722 cm$^{-1}$ |
| 9 | A12 | 2.66 | 46 | 10.2 | 3.14 | 119 | 21 | II | P—Ch:M (19:1) | 0.83 | +25° | 1724 cm$^{-1}$ |
| 10 | A13 | 6 | 100[2] | 6.5 | 8.65 | — | 50 | I | P—Ch:M (9:1) | 0.55[3] | +8° | 1726 cm$^{-1}$ |

[1]Diethyl ether used in place of ethyl acetate.
[2]Dioxan used in place of ethanol.
[3]Only a portion of the product was purified.

EXAMPLE 11

Methyl 11α-cyclohexylamino-3α-hydroxy-2β-methoxy-5α-androstane-17β-carboxylate

A suspension of the product of Example A3 (1.512 g) in ethanol (15 ml) and cyclohexanone (1.5 ml) was stirred with sodium cyanoborohydride (1.5 g) for 24 h. 5% NaHCO$_3$ solution was added and then water. The mixture was extracted with ether (x2) and the extract was washed with water, dried and evaporated to leave a froth which was purified by column chromatography using chloroform:methanol (19:1) and crystallised from acetonitrile to give the title compound (1.069 g), m.p. 143°–145° C., $[\alpha]_D$+9.5°.

EXAMPLE 12

Methyl 11α-cyclohexylamino-3α-hydroxy-5α-androstane-17β-carboxylate

Sodium cyanoborohydride (2 g) was added to a mixture of the product of Example A2 (2 g) and cyclohexanone (2.5 ml) in ethanol (30 ml). The mixture was kept at 21° C. for 5 h. 5% NaHCO$_3$ solution and water were added and the mixture was extracted with ether (x2). The extract was washed with water, dried and evaporated to leave a froth which was purified by column and preparative layer chromatography using CHCl$_3$:MeOH (9:1) to give the title compound (0.763 g) as a froth, $[\alpha]_D$+6°, $\nu_{max}$ 1720 cm$^{-1}$.

EXAMPLES 13–25

Table 6 summarises the preparation of 11α-alkylamino compounds from the corresponding 11α-amines using the general method of Examples 11 and 12.

The aldehydes/ketones used in Examples 13–25 were as follows: cyclohexanone (Examples 13, 15, 20 and 22); cyclopentanone (Examples 16 and 17); 3,3-dimethylbutyraldehyde (Example 14); hexaldehyde (Example 18); 4-methylpentanal (Example 19); 3-methylbutanal (Example 21); cycloheptanone (Example 23); cyclobutanone (Example 24) and acetone (Example 25).

Purification was effected by Preparative t.l.c. (P), column chromatography (C) or crystallisation (X).

The following compounds were prepared:
13. Ethyl 11α-cyclohexylamino-2β-ethoxy-3α-hydroxy- 5α-androstane-17β-carboxylate,
14. Methyl 11α-(3,3-dimethylbutylamino)-2β-ethoxy-3α-hydroxy-5α-androstane-17β-carboxylate,
15. Methyl 11α-cyclohexylamino-2β-ethoxy-3α-hydroxy-5α-androstane-17β-carboxylate,
16. Methyl 11α-cyclopentylamino-3α-hydroxy-5α-androstane-17β-carboxylate,
17. Methyl 11α-cyclopentylamino-3α-hydroxy-2β-methoxy-5α-androstane-17β-carboxylate,
18. Methyl 2β-ethoxy-11α-hexylamino-3α-hydroxy-5α-androstane-17β-carboxylate,
19. Methyl 2β-ethoxy-3α-hydroxy-11α-(4-methylpentyl-amino)-5α-androstane-17β-carboxylate,
20. Methyl 11α-cyclohexylamino-3α-hydroxy-5β-androstane-17β-carboxylate,
21. Methyl 2β-acetoxy-3α-hydroxy-11α-(3-methylbutylamino)-5α-androstane-17β-carboxylate,
22. Methyl 2β-acetoxy-11α-cyclohexylamino-3α-hydroxy-5α-androstane-17β-carboxylate,
23. Methyl 11α-cycloheptylamino-3α-hydroxy-2β-methoxy-5α-androstane-17β-carboxylate,
24. Methyl 11α-cyclobutylamino-3α-hydroxy-2β-methoxy-5α-androstane-17β-carboxylate,
25. Methyl 2β-ethoxy-3α-hydroxy-11α-(1-methylethyl-amino)-5α-androstane-17β-carboxylate.

TABLE 6

| Ex. No. | Starting Material Ex. No. | Wt (g) | Ethanol (ml) | Aldehyde/ Ketone (ml) | NaBH$_3$CN (g) | Reaction Time (h) | Purification System | Yield (g) | $[\alpha]_D$ | m.p./ $\nu_{max}$ |
|---|---|---|---|---|---|---|---|---|---|---|
| 13[1] | A4 | 2.0 | 20 | 2.5 | 3.07 | 27 | C—Ch:M (19:1) X—A | 1.31 | +5° | 109–115° C. |
| 14 | A1 | 2.5 | 25 | 1.5 | 2.63 | 17 | C—Ch:M (19:1) X—A | 1.01 | +16° | 82.5–85.5° C. |
| 15 | A1 | 2.5 | 25 | 2.6 | 2.57 | 20 | C—Ch:M (19:1) X—A | 1.51 | +6° | 111–114° C. |
| 16[2] | A2 | 2.0 | 20 | 2.0 | 2.0 | 19 | C and P Ch:M (9:1) | 1.47 | +12° | 1724 cm$^{-1}$ |
| 17[3] | A3 | 0.96 | 10 | 1.0 | 1.5 | 23 | X—A | 0.62 | +16.5° | 130–132° C. |
| 18 | A1 | 2.49 | 30 | 2.0 | 2.49 | 2 | C—Ch:M (19:1) X—A | 1.12 | +21° | 108–109° C. |

TABLE 6-continued

| Ex. No. | Starting Material Ex. No. | Wt (g) | Ethanol (ml) | Aldehyde/ Ketone (ml) | NaBH3CN (g) | Reaction Time (h) | Purification System | Yield (g) | $[\alpha]_D$ | m.p./ $\nu_{max}$ |
|---|---|---|---|---|---|---|---|---|---|---|
| 19[1] | A1 | 2.61 | 20 | 3.0 | 2.40 | 70 | X—A | 1.04 | +21° | 123–125° C. |
| 20 | A13 | 2.51 | 30 | 2.9 | 2.51 | 5 | P—Ch:M (19:1) | 2.54 | −9° | 1725 cm$^{-1}$ |
| 21 | A14 | 2.85 | 40 | 4.2 | 3.0 | 20 | C—Ch:M (9:1) X—A | 0.27[4] | +24.2° | 117–120° C. |
| 22 | A14 | 4.08 | 40 | 4.0 | 4.0 | 27 | C—Ch:M (19:1) | 0.86 | +10.6° | 1722 cm$^{-1}$ |
| 23[5] | A3 | 2.7 | 27 | 2.7 | 2.7 | 45.5 | C—Ch:M (19:1) P—Ch:M (9:1) X—A | 0.43 | +8° | 100–103° C. |
| 24 | A3 | 2.8 | 30 | 1.0 | 2.8 | 47 | C—Ch:M (19:1) P—Ch:M (9:1) | 0.64 | +26° | 1720 cm$^{-1}$ |
| 25 | A1 | 1.0 | 15 | 6.0 | 1.0 | 94 | C—Ch:M (19:1) | 0.44 | +16.5° | 1723 cm$^{-1}$ |

Notes for Table 6
[1]An additional work up was used, as follows:
The product after evaporation of the ether extract was dissolved in 2M—HCl, water and ethanol and the solution washed with ether. The ethereal wash was extracted with M—HCl and water and the total aqueous phase brought to pH 10 with 0.88 NH3 solution and extracted with ether. The extract was then washed, dried and evaporated to give a residue which was subjected to purification.
[2]Sodium borohydride (0.05 g) added after 18h.
[3]Sodium borohydride (0.01 g) added after 22h.
[4]Only a portion of the product was purified.
[5]Sodium borohydride (0.15 g) added after 45h.

EXAMPLE 26

Propyl 2β-ethoxy-3α-hydroxy-11α-(3-methylbutylamino)-5α-androstane-17β-carboxylate A solution of the product of Example B1 (0.9 g) in propan-1-ol (20 ml) was heated at 100° C. with concentrated H2SO4 (4 ml) for 24 h. The cooled mixture was brought to pH 9 with 5% NaHCO3 solution and extracted with ether (x2). The extract was washed with water, dried and evaporated to leave an oil which was purified by preparative t.l.c. using chloroform:methanol (9:1) to give the title compound (0.612 g) as an oil, $[\alpha]_D+22°$, $\nu_{max}$ 1720 cm$^{-1}$.

EXAMPLE 27

Cyclohexyl 2β-ethoxy-3α-hydroxy-11α-(3-methylbutylamino)-5α-androstane-17β-carboxylate A solution of the product of Example B1 (4.26 g) in cyclohexanol (30 ml) was stirred at 110° C. with concentrated H2SO4 (2 ml) for 18 h. The mixture was brought to basic pH with 0.88 NH3 solution and extracted with ether (2x). The extract was washed with water, dried and evaporated to leave an oil which was purified by column chromatography eluted with EtOAc/MeOH (3:1) and CHCl3:MeOH (19:1) to give the title compound (857 mg) $[\alpha]_D+11°$, $\nu_{max}$ 1713 cm$^{-1}$.

EXAMPLE 28

Methyl 11α-cyclohexylamino-2β-ethoxy-3α-hydroxy-5α-androstane-17β-carboxylate

Bromine (0.44 ml) was added to a stirred solution of sodium hydroxide (1.24 g) in water (8 ml) at 0° C. Dioxan (4 ml) was added and this mixture was added to a solution of Intermediate 36 (0.584 g) in dioxan (25 ml) and water (8 ml) at 10° C. The mixture was stirred at room temperature for 3 h. Sodium metabisulphite (2 g) was added and after 10 minutes the mixture was diluted with water (100 ml). The solvents were removed by evaporation to leave a solid which was dissolved in methanol (30 ml) and the solution was heated at reflux with concentrated H2SO4 (1 ml) for 5 h. The mixture was brought to pH 10 with 0.88 NH3 solution and diluted with water (150 ml). The precipitate was extracted wit ether (x3) and the extract was washed with water (100 ml), dried and evaporated to leave an oil which was purified by column chromatography eluted with CHCl3:MeOH (9:1) to leave an oil which was crystallised from acetonitrile to give the title compound (0.235 g), m.p. and mixed m.p. 110°–112° C., $[\alpha]_D+13°$.

EXAMPLE 29

Methyl 2β-ethoxy-3α-hydroxy-11α-(3-methylbutylamino)-5α-androstane-17β-carboxylate Methanol (2 ml) and dicyclohexylcarbodiimide (100 mg) were added to a stirred mixture of the product of Example A17 (221 mg) in ether (20 ml) to give a solution. 4-Dimethylaminopyridine (10 mg) was added and the mixture was stirred for 72 h. The mixture was filtered and the filtrate was evaporated to leave a froth. This was purified by column chromatography on silica eluted with CHCl3:MeOH (19:1) to give the title compound (130 mg) which crystallised from acetonitrile, m.p. 123°–125° C., $[\alpha]_D+18°$.

EXAMPLE 30

Methyl 2β-ethoxy-3α-hydroxy-11α-(3-methylbutylamino)-5α-androstane-17β-carboxylate Concentrated H2SO4 (10 drops) was added to a solution of the product of Example B3 (75 mg) in methanol (3 ml) and the mixture was brought to reflux and heated for 6 h. The cooled mixture was brought to pH with 0.88 NH3 solution, diluted with water (50 ml) and extracted with ether (x3). The extract was washed with water, dried and evaporated to leave an oil (70 mg) which was crystallised from acetonitrile to give the title compound (40 mg) m.p. and mixed m.p. 123°–125° C., $[\alpha]_D+21°$.

EXAMPLE 31

Methyl 2β-ethoxy-3α-hydroxy-11α-(3-methylbutylamino)-5α-androstane-17β-carboxylate A solution of diazomethane in ether was added to a solution of the product of Example A17 (550 mg) in ether (20 ml) and tetrahydrofuran (20 ml). After 0.5 h glacial acetic acid (2 drops) was added and the mixture was brought to pH 10 with 0.88 NH₃ solution and diluted with water (100 ml). The organic phase was washed with water and the combined aqueous phase was extracted with ether. The total organic phase was washed with water, dried and evaporated to leave an oil which was purified by column chromatography eluted with CHCl₃:MeOH (19:1) and the product was crystallised from acetonitrile to give the title compound (57 mg) m.p. 123°–125° C., $[\alpha]_D+21°$.

EXAMPLE 32

Methyl 2β-ethoxy-3α-hydroxy-11α-(3-methlbutylamino)-5α-androstane-17β-carboxylate Concentrated H₂SO₄ (1 ml) was added to a solution of the product of Example A17 (500 mg) in methanol (20 ml) and the mixture was heated at reflux for 6 h. The cooled mixture was brought to pH 10 with 0.88 NH₃ solution and diluted with water (150 ml). The precipitate was extracted with ether (x3) and the extract was washed with water, dried and evaporated to leave an oil which was crystallised from acetonitrile to give the title compound (245 mg) m.p. 123°–125° C. $[\alpha]_D+23°$.

EXAMPLE 33

Methyl 11α-cyclohexylamino-3α-hydroxy-2β-methoxy-5α-androstane-17β-carboxylate

Boron trifluoride diethyl etherate (0.2 ml) was added to a suspension of Intermediate 17 (354 mg) in methanol (5 ml). The mixture was stirred for 1.75 h, diluted with 5% NaHCO₃ solution and extracted with ether (x3). The extract was washed with water, dried and evaporated to leave a foam which was purified by preparative t.l.c. in CHCl₃:MeOH (9:1) to give a foam which crystallised from acetonitrile to give the title compound (56 mg) m.p. 141°–143° C., $[\alpha]_D+10°$.

EXAMPLE 34

Methyl 11α-cyclohexylamino-3α-hydroxy-5α-androstane-17β-carboxylate

Diethyl azodicarboxylate (470 mg) was added to a mixture of triphenylphosphine (790 mg), formic acid (0.11 ml) and Intermediate 32 (432 mg) in dry THF (10 ml). The mixture was left for 20 h, brought to basic pH with 5% NaHCO₃ solution and extracted with ethyl acetate (x3). The extract was washed with water, dried and evaporated to leave a solid which was partially purified by preparative t.l.c. in CHCl₃:MeOH (19:1) to give an oil. The oil was dissolved in ethyl acetate and the solution was extracted with 2 M-HCl solution (x3) and water (x3). The extract was brought to pH 10 to 0.88 NH₃ solution and the precipitate was extracted with ethyl acetate (x4). The extract was dried and evaporated to leave a foam which was purified by preparative t.l.c. in CHCl₃:MeOH (9:1) to give the title compound (67 mg) $[\alpha]_D+4°$.

EXAMPLE 35

Methyl 11α-cyclohexylamino-3α-hydroxy-5α-androstane-17β-carboxylate

Chloroiridic acid reagent (16 ml) was brought to pH 7 with triethylamine and Intermediate 34 (860 mg) was dissolved in it. The solution was heated at reflux for 27 h, cooled and brought to pH 9 with 0.88 NH₃ solution. Water (30 ml) was added and the mixture was extracted with ethyl acetate (x3). The extract was washed with water, dried and evaporated to leave a foam which was purified by preparative t.l.c. in CHCl₃:MeOH (5:1) to give the title compound (248 mg) $[\alpha]_D+6°$.

EXAMPLES 36–62

Table 7 summarises the preparation of the hydrochloride salts.

A solution of hydrochloric acid in water was added to the base or a suspension of the base in any additional water and the mixture was stirred or shaken until either a clear solution was obtained or no more base dissolved. The mixture was made up to the appropriate weight or volume with water and filtered and any undissolved base was collected, dried and weighed to determine the solution concentrations. The pH was measured.

TABLE 7

| Example No | Example No of free base | Wt (mg) | HCl M | HCl Vol (ml) | Additional Water (ml) | Total Weight or Volume | Solid residue (mg) | pH | Conc'n. (%) |
|---|---|---|---|---|---|---|---|---|---|
| 36 | B1 | 300 | 0.0963 | 6.7 | 9 | 20 ml | — | 2.7 | 1.5 |
| 37 | B3 | 301 | 0.0963 | 6.6 | 9 | 20 ml | — | 3.2 | 1.5 |
| 38 | B13 | 100 | 0.0924 | 2.2 | 5 | 10 ml | — | 3.2 | 1 |
| 39 | B2 | 993 | 0.0979 | 21.8 | — | 125.03 g | 83 | 3.0 | 0.73 |
| 40 | B9 | 674 | 0.0979 | 14.0 | — | 49.98 g | 40 | 3.2 | 1.27 |
| 41 | B11 | 100.8 | 0.0979 | 2.23 | — | 10.03 g | — | 3.1 | 1.0 |
| 42 | B17 | 100.6 | 0.0979 | 2.3 | — | 10.02 g | — | 3.7 | 1.0 |
| 43 | B12 | 100 | 0.0979 | 2.4 | — | 10 ml | — | 2.1 | 1.0 |
| 44 | B16 | 100 | 0.0979 | 2.44 | — | 10 ml | — | 3.0 | 1.0 |
| 45 | B8 | 100 | 0.0979 | 2.34 | — | 10 ml | — | 2.5 | 1.0 |
| 46 | B26 | 100 | 0.0979 | 2.08 | 7 | 10 ml | — | 2.95 | 1.0 |
| 47 | B18 | 100 | 0.0979 | 2.14 | 5 | 10 ml | — | 3.4 | 1.0 |
| 48 | B19 | 100 | 0.0979 | 2.14 | 5 | 10 ml | — | 3.4 | 1.0 |
| 49 | B10 | 100 | 0.0979 | 2.44 | 6 | 10 ml | — | 3.2 | 1.0 |
| 50 | B4 | 284.3 | 0.0924 | 6.26 | — | 20.1 g | 135 | 2.3 | 0.76 |
| 51 | B5 | 220.6 | 0.0924 | 4.72 | — | 20.04 g | 41 | 3.15 | 0.9 |
| 52 | B6 | 610.3 | 0.0924 | 12.7 | — | 40.01 g | 339 | 2.5 | 0.68 |
| 53 | B15 | 100 | 0.0924 | 2.28 | 6 | 10 ml | — | 3.05 | 1.0 |
| 54 | B14 | 100 | 0.0924 | 2.27 | 6 | 10 ml | — | 3.15 | 1.0 |
| 55 | B7 | 100 | 0.0924 | 2.6 | — | 10 ml | — | 2.75 | 1.0 |
| 56 | B22 | 100 | 0.0979 | 2.09 | — | 10 g | — | 4.0 | 1.0 |

TABLE 7-continued

| Example No | Example No of free base | Wt (mg) | HCl M | HCl Vol (ml) | Additional Water (ml) | Total Weight or Volume | Solid residue (mg) | pH | Conc'n. (%) |
|---|---|---|---|---|---|---|---|---|---|
| 57 | B21 | 100.5 | 0.0979 | 2.15 | — | 10 g | — | 4.3 | 1.0 |
| 58 | B20 | 100 | 0.0979 | 2.37 | 5 | 10 ml | — | 3.0 | 1 |
| 59 | B27 | 100 | 0.0979 | 1.92 | 15 | 20 ml | 28 | 2.6 | 0.37 |
| 60 | B23 | 101.2 | 0.1076 | 1.98 | — | 10 g | — | 5.3 | 1.0 |
| 61 | B24 | 100 | 0.1076 | 2.14 | — | 10 ml | 10 | 2.2 | 0.9 |
| 62 | B25 | 100.8 | 0.1076 | 2.15 | — | 10 g | — | 2.4 | 1.0 |

EXAMPLES 63–67

Table 8 summarises the preparation of salts of methyl 2$\beta$-ethoxy-3$\alpha$-hydroxy-11$\alpha$-(3-methylbutylamino)-5$\alpha$-androstane-17$\beta$-carboxylate.

The appropriate acid was added to a suspension of the free base (50 mg) in water (4 ml) and the mixture was stirred or shaken until a clear solution was obtained. The solution was made up to 5 ml with water to give a 1% solution and the pH was measured.

TABLE 8

| Example No. | Acid | Vol or wt. | pH |
|---|---|---|---|
| 63 | Citric acid hydrate | 22.7 mg | 3.65 |
| 64 | Maleic acid | 12.5 mg | 4.55 |
| 65 | Ascorbic acid | 37.98 mg | 4.10 |
| 66 | Sulphuric acid (0.1M) | 0.54 ml | 2.90 |
| 67 | Glutaric acid | 14.2 mg | 4.70 |

The following Examples illustrate pharmaceutical formulations of the compounds according to the invention.

EXAMPLE A

| Tablet - wet Granulated | mg/tablet |
|---|---|
| Methyl 11$\alpha$-cyclohexylamino-3$\alpha$-hydroxy-2$\beta$-methoxy-5$\alpha$-androstane-17$\beta$-carboxylate hydrochloride | 27.0 |
| Lactose | 93.0 |
| Maize Starch | 50.0 |
| Polyvinyl pyrrolidone | 2.0 |
| Sodium starch glycolate | 6.0 |
| Magnesium stearate | 2.0 |
| Tablet weight | 180.0 mg |

Sieve the steroid and maize starch through a 40 mesh screen. Blend the maize starch with the steroid in a suitable blender. Make a 5–10% w/v aqueous solution of the polyvinyl pyrrolidone. Add this solution to the mixing powder and mix until granulated. Pass the granulate through a number 12 screen. Dry the granules at 50° C. in an oven or in a fluid bed dryer. Screen the dry granules through a 16 mesh screen, and blend in the sodium starch glycolate and magnesium stearate previously sieved through a 60 mesh screen. Compress on appropriate punches on an automatic tablet machine.

EXAMPLE B

| Tablet - Direct compression | mg/tablet |
|---|---|
| Methyl 11$\alpha$-cyclohexylamino-3$\alpha$-hydroxy-2$\beta$-methoxy-5$\alpha$-androstane-17$\beta$-carboxylate hydrochloride | 27.0 |
| Microcrystalline cellulose | 135.0 |
| Sodium starch glycolate | 6.0 |
| Magnesium stearate | 2.0 |
| | 170.0 mg |

Sieve the steroid and microcrystalline cellulose through a 40 mesh sieve. Sieve the sodium starch glycolate and magnesium stearate through a 60 mesh sieve. Blend the powders together in a suitable blender until homogeneous. Compress on appropriate punches on an automatic tablet press.

The tablets, made in either Example A or B, may be covered in a thin polymer coat applied by the usual film coating techniques. A pigment may be included in the film coat.

EXAMPLE C

| Hard gelatin capsule | mg/capsule |
|---|---|
| Methyl 2$\beta$-ethoxy-3$\alpha$-hydroxy-11$\alpha$-(3-methylbutylamino)-5$\alpha$-androstane-17$\beta$-Carboxylate hydrochloride | 54.0 |
| Lactose, anhydrous | 141.0 |
| Sodium starch glycolate | 4.0 |
| Magnesium stearate | 1.0 |
| Capsule fill weight | 200.0 mg |

The steroid is sieved and blended by a gradual dilution technique with the sieved excipients, in a suitable blender. The blend is then filled into suitable size hard gelatin capsule shells using an automatic machine.

EXAMPLE D

| Tablet - Wet granulated | mg/tablet |
|---|---|
| Methyl 2$\beta$-ethoxy-3$\alpha$-hydroxy-11$\alpha$-(3-methylbutylamino)-5$\alpha$-androstane-17$\beta$-carboxylate hydrochloride | 108.00 |
| Maize starch | 138.0 |
| Polyvinyl pyrrolidone | 2.5 |
| Sodium starch glycolate | 7.5 |
| Magnesium stearate | 2.0 |
| Tablet weigth | 258.00 |

The method of manufacture is as in Example A.

The tablets may be coated in a thin polymeric coat applied by the usual techniques. The film coat may contain a pigment.

EXAMPLE E

Intravenous Injections
Ingredients:
Methyl 11$\alpha$-cyclohexylamino-3$\alpha$-hydroxy-2$\beta$-methoxy-5$\alpha$-androstane-17$\beta$-carboxylate hydrochloride or methyl 2$\beta$-ethoxy-3$\alpha$-hydroxy-11$\alpha$-(3-methylbutylamino)-5α-androstane-17β-carboxylate hydrochloride (equivalent to 1 to 10 mg of free base)

Sodium chloride sufficient for isotonicity Water for Injections to 1 ml

Dissolve the steriod and the sodium chloride in some of the water. If necessary adjust the pH with sodium hydroxide solution or hydrochloric acid solution. Make up to volume with water and stir until homogeneous. Filter the solution into clean glass vials and seal by fusion. The solution may be sterilised by autoclaving or filtration or preparing under aseptic conditions.

We claim:

1. Compounds of the formula:

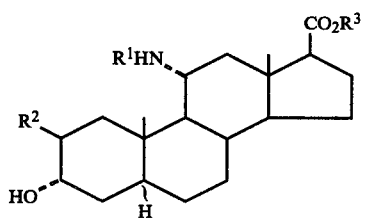

wherein:

$R^1$ is a $C_{1-8}$ alkyl group or a $C_{3-7}$ cycloalkyl group;

$R^2$ is a hydrogen atom, a $C_{1-6}$ alkoxy group or a $C_{2-5}$ alkanoyloxy group; and $R^3$ is a $C_{1-8}$ alkyl group or a $C_{3-7}$ cycloalkyl group; provided that when the compounds contain a 5β-hydrogen atom, $R^2$ is a hydrogen atom, and the D-homo analogues thereof having the group —$CO_2R^3$ (wherein $R^3$ is as defined above) at the 17aβ-position, and acid addition salts thereof.

2. Compounds as claimed in claim 1 wherein: $R^1$ is an isopentyl, hexyl, isohexyl, neohexyl, cyclopentyl or cyclohexyl group, $R^2$ is a hydrogen atom or a methoxy, ethoxy or propoxy group and $R^3$ is a methyl or ethyl group, having a 5α-hydrogen atom and wherein ring D has 5 members.

3. Compounds as claimed in either of claims 1 and 2 in the form of physiologically acceptable acid addition salts.

4. Compounds as claimed in claim 3 in the form of hydrochlorides, hydrobromides, phosphates, sulphates, p-toluenesulphonates, methanesulphonates, citrates, tartrates, acetates, ascorbates, lactates, maleates, succinates, tricarballylates, glutarates and glutaconates.

5. A compound as claimed in claim 1 which is methyl 2β-ethoxy-3α-hydroxy-11α-(3-methylbutylamino)-5α-androstane-17β-carboxylate, and its physiologically acceptable acid addition salts.

6. A compound as claimed in claim 1 which is methyl 2β-methoxy-3α-hydroxy-11α-(3-methylbutylamino)-5α-androstane-17β-carboxylate, and its physiologically acceptable acid addition salts.

7. A compound as claimed in claim 1 which is methyl 11α-cyclohexylamino-3α-hydroxy-2β-methoxy-5α-androstane-17β-carboxylate, and its physiologically acceptable acid addition salts.

8. A compound as claimed in claim 1 which is methyl 11α-cyclohexylamino-3α-hydroxy-5α-androstane-17β-carboxylate, and its physiologically acceptable acid addition salts.

9. Compounds as claimed in any of claims 5 to 8 in the form of their hydrochlorides.

10. Pharmaceutical compositions comprising at least one compound of formula (I) as claimed in claim 1 or a physiologically acceptable acid addition salt thereof in admixture with one or more pharmaceutical carriers or excipients.

11. A process for the manufacture of a compound of the formula (I) as claimed in claim 1 including (A) reacting a corresponding 11α-amino compound or a corresponding 11α-amino-17β-carboxylic acid with a compound of formula $R^1X$ wherein $R^1$ is as defined in claim 1 and X is a readily displaceable atom or group;

(B) (where a 2β-substituted 5α-compound is desired) treating a corresponding 2α,3α-epoxide with a compound $HR^2$ under acidic conditions or a compound which produces the anion $(R^2)^-$ wherein $R^2$ is as defined in claims 1 other then hydrogen, and then, when the initial product possesses a deprotonated 3α-hydroxy group, treating the product obtained with a source of protons;

(C) reacting a corresponding 11α-amino compound in the presence of a reducing agent with a monocarbonyl compound serving to introduce the group $R^1$;

(D) (where a 2β-unsubstituted compound is desired) reducing with a suitable reducing agent a corresponding 3-oxo compound;

(E) converting a corresponding N,N-disubstituted 11α-amino compound into a N-monosubstituted compound;

(F) esterifying a corresponding 17β-carboxylic acid;

(g) reacting a corresponding $\Delta^{16}$-compound with a suitable reducing agent;

(H) transesterifying a corresponding compound having a 17β-ester group other than the desired group $R^3$ (as defined in claim 1) with an alcohol of formula $R^3OH$ (wherein $R^3$ is as defined in claim 1);

(I) inverting a corresponding 3β-hydroxy compound; or (J) deprotecting a corresponding compound having a protected 3α-hydroxy group, followed where necessary, by the formation of acid addition salts.

12. Compounds of formula:

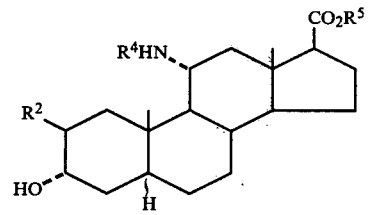

(wherein $R^2$ is as defined in claim 1 (provided that when the compounds contain a 5β-hydrogen atom, $R^2$ is a hydrogen atom);

$R^4$ is a hydrogen atom or a group $R^1$ as defined in claim 1; and $R^5$ is a hydrogen atom or a group $R^3$ as defined in claim 1;

provided that at least one of $R^4$ and $R^5$ is a hydrogen atom and the D-homo analogues thereof having the group —$CO_2R^5$ at the 17aβ-position and salts and zwitterionic forms thereof.

13. A method of treatment or prophylaxis of a human or animal subject suffering from or liable to ventricular dysrhythmias which comprises administering to said subject an effective amount of one or more compounds as claimed in claim 1.

* * * * *